US007662065B1

(12) United States Patent
Kahn et al.

(10) Patent No.: US 7,662,065 B1
(45) Date of Patent: Feb. 16, 2010

(54) METHOD AND APPARATUS TO PROVIDE DAILY GOALS IN ACCORDANCE WITH HISTORICAL DATA

(75) Inventors: Philippe Kahn, Aptos, CA (US); Arthur Kinsolving, Santa Cruz, CA (US); Derek Conrad Keil, Troy, NY (US)

(73) Assignee: DP Technologies, Inc., Scotts Valley, CA (US)

( * ) Notice: Subject to any disclaimer, the term of this patent is extended or adjusted under 35 U.S.C. 154(b) by 22 days.

(21) Appl. No.: 11/515,068

(22) Filed: Sep. 1, 2006

(51) Int. Cl.
*A63B 71/00* (2006.01)
*A63B 69/00* (2006.01)
(52) U.S. Cl. .................. 482/9; 482/8; 434/247
(58) Field of Classification Search ............. 482/1, 482/2, 8, 9, 901, 902, 3, 201; 434/247, 236, 434/238
See application file for complete search history.

(56) References Cited

U.S. PATENT DOCUMENTS

| | | | | |
|---|---|---|---|---|
| 6,013,008 A * | 1/2000 | Fukushima | .................. | 482/8 |
| 6,837,827 B1 * | 1/2005 | Lee et al. | .................. | 482/8 |
| 6,866,613 B1 * | 3/2005 | Brown et al. | .................. | 482/8 |
| 7,063,644 B2 * | 6/2006 | Albert et al. | .................. | 482/8 |
| 7,070,539 B2 * | 7/2006 | Brown et al. | .................. | 482/8 |
| 2005/0164837 A1 * | 7/2005 | Anderson et al. | ............. | 482/52 |
| 2005/0172311 A1 * | 8/2005 | Hjelt et al. | .................. | 725/10 |
| 2005/0288154 A1 * | 12/2005 | Lee et al. | .................. | 482/3 |
| 2006/0136173 A1 * | 6/2006 | Case et al. | .................. | 702/182 |

* cited by examiner

*Primary Examiner*—Loan H Thanh
*Assistant Examiner*—Sandhara M Ganesan
(74) *Attorney, Agent, or Firm*—Blakely, Sokoloff, Taylor & Zafman, LLP; Judith A. Szepesi (57) ABSTRACT

A method and apparatus for identifying a raw target exercise level for a user and applying a goal setting algorithm to adjust the raw target exercise level for the user, the adjustment made in accordance with analysis of the user's data, and displaying an adjusted target exercise level to the user, in order to achieve the raw target exercise level for the user.

21 Claims, 9 Drawing Sheets

Goal Setting Algorithms
- Display target above actual target, for users motivated by hard to achieve goals
- Display target below actual target, for users motivated by exceeding goals
- Display target at actual target, for users motivated by realistic goals Sub-Algorithms #1
- Moving most of target to before likely time to exercise, for people who usually run late & work hard to catch up
- Moving most of target exercise to actual likely time to exercise, for people who want to use goals to schedule their day Sub-Algorithm #2
- Setting morning exercise targets for people who exercise in the morning
- Setting other time exercise targets, based on data regarding user's exercise habits Sub-Algorithm #3
- Setting targets based on health-based levels of motion throughout the day Sub-Algorithm #4
- Adjusting targets based on other health data from the user
-

.
.
.

Sub-Algorithm #n
- Other adjustments to daily target alpine graph

Fig. 8

METHOD AND APPARATUS TO PROVIDE DAILY GOALS IN ACCORDANCE WITH HISTORICAL DATA

FIELD OF THE INVENTION

The present invention relates to goal setting, and more particularly for setting daily goals.

BACKGROUND

As obesity and related diseases skyrocket throughout the Western world, the search is on for a solution that would help people manage their weight and activity level. The problem is real, and it primarily relates to eating too much and exercising or moving too little. With more jobs being stationary, more people driving to and from work, more work-saving devices in the home, most people's built-in exercise level is declining rapidly.

There are numerous tools available that attempt to promote exercise. They generally set a daily goal for the individual. For example, there are tools that set daily goals for pedometer users, such as 10,000 steps per day. This is a recommended level. However, these tools do not take other factors into consideration, but rather make a set determination either based on user selection or based on generic medical recommendations.

SUMMARY OF THE INVENTION

A method comprising of identifying a raw target exercise level for a user and applying a goal setting algorithm to adjust the raw target exercise level for the user, the adjustment made in accordance with analysis of the user's data, and displaying an adjusted target exercise level to the user, in order to achieve the raw target exercise level for the user.

BRIEF DESCRIPTION OF THE DRAWINGS

The present invention is illustrated by way of example, and not by way of limitation, in the figures of the accompanying drawings and in which like reference numerals refer to similar elements and in which.

DETAILED DESCRIPTION

The method and apparatus described is used to set activity goals for a user. In one embodiment, the goals may be set for steps for a user utilizing a pedometer. Appropriate goals may be set for other types of exercise measurement. For example, the system may utilize distance for a bicyclist or treadmill walker, calories expended for elliptical exercise user or rower, or another logical measurement of activity for another device. In one embodiment, the system automatically receives data from the appropriate device, i.e., exercise equipment or pedometer. Alternatively, in one embodiment, the user may enter the data manually into the system with a computer or mobile device (mobile phone, pocket computer, voice to text device, etc.) The system sets daily goals for the user. The goals, in one embodiment, may be illustrated using a progress graph, showing the goals throughout the day. Instead of setting a single goal to be reached by the end of the day, the system, in one embodiment, sets smaller goals throughout the day. This helps a user not put off the exercise until the last minute. The goals throughout the day are set based on user data. In one embodiment, user data may include historical data of use performance, knowledge of the user's motivational structure, as well as health data.

Figure 1A:
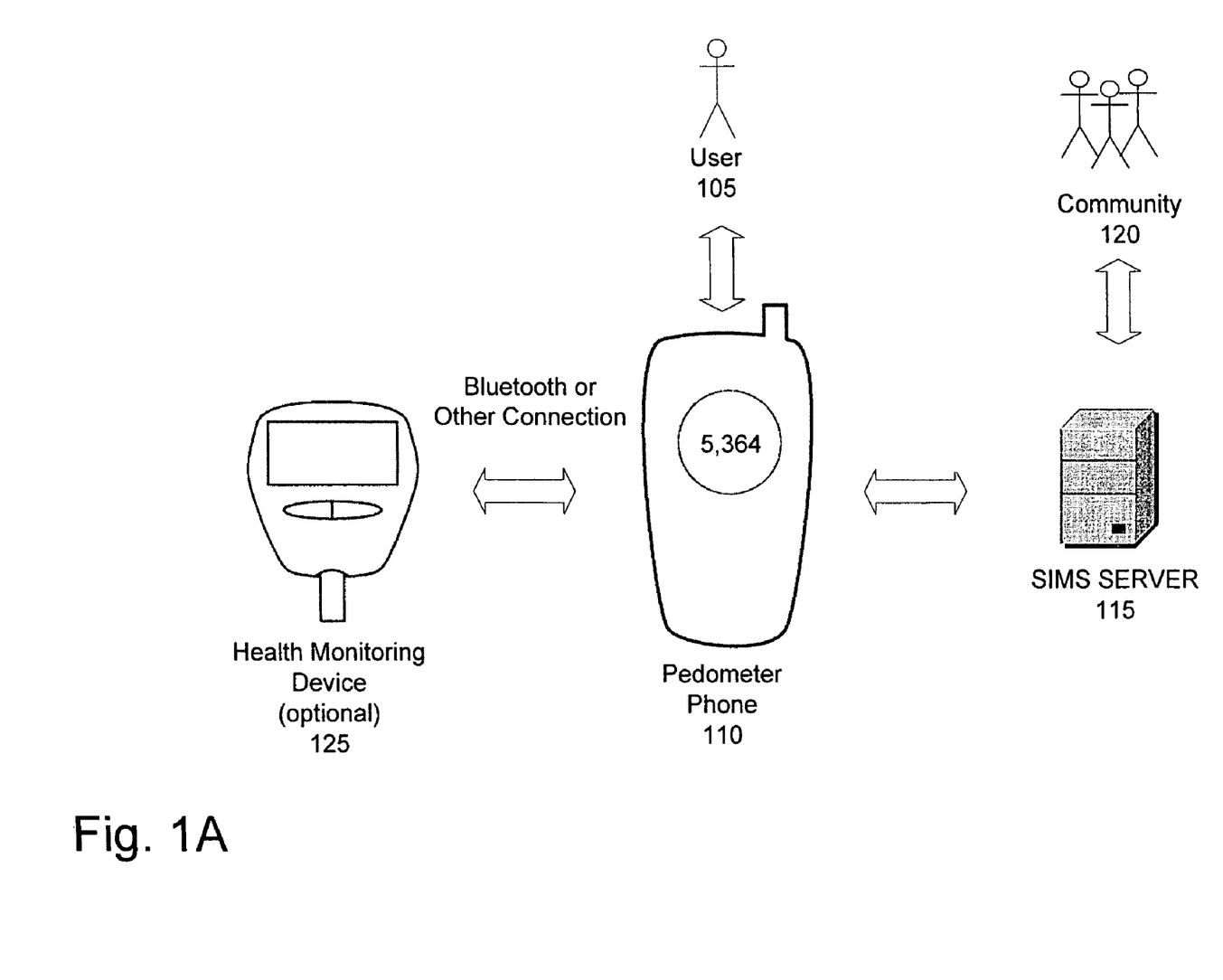
FIG. 1A illustrates the general relationship between the various systems and the user.
Figure 4:
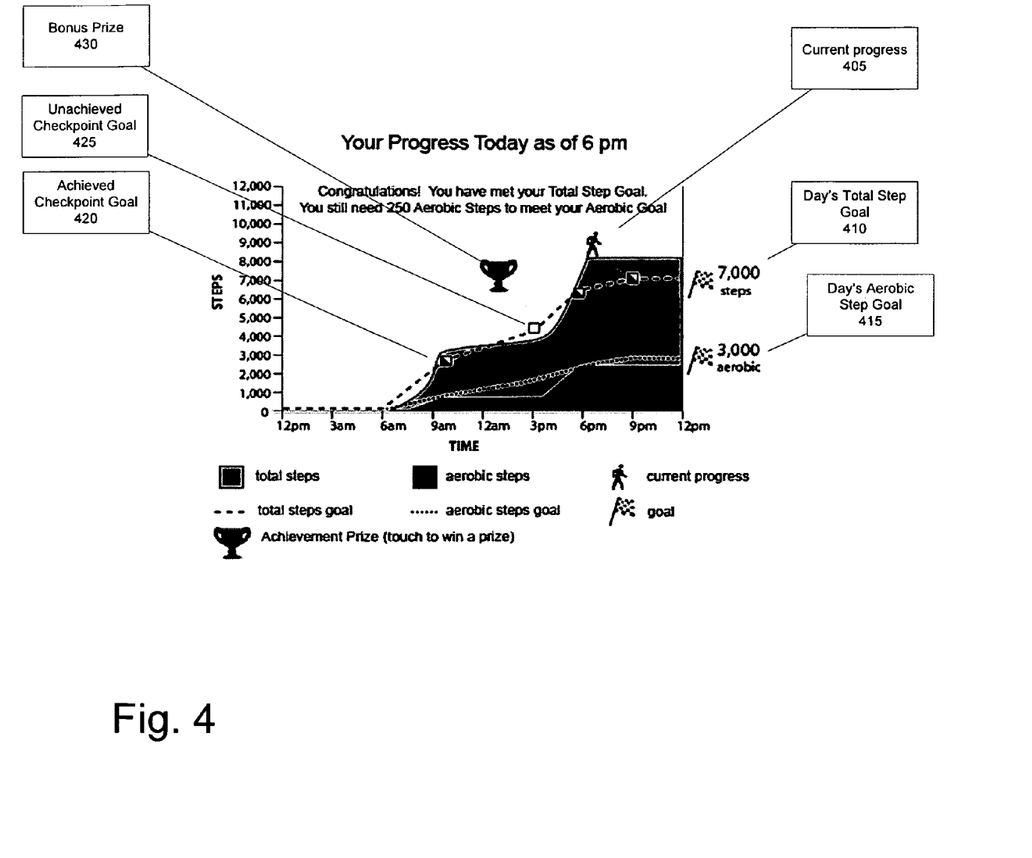
FIG. 4 is an illustration of one embodiment of a progress graph showing goals through the day.

FIG. 1A illustrates the general relationship between the various systems and the user. The user 105 carries a phone with an integrated step counter 110, which communicates the user's step count to a SIMS server 115. The SIMS server 115 shares this data with a community 120, to provide further motivation for the user to keep up with the exercise program. The step counting phone 110 provides the goal data to the user. In one embodiment, the step counting phone 110 displays the goals, throughout the day, as shown in FIG. 4. Alternatively, the step counting phone may simply display goals such as "Achieved: 2,000 steps, Goal: 2,200."

In one embodiment, the step counting phone 110 may be used to transmit other health information to the SIMS server 115. The phone 110 may interface with other health devices 125 to transmit their information to the SIMS server 115. Alternatively, the health monitoring device 125 may transmit its data to the SIMS server 115 through other means. Alternatively, the user, or an authorized individual, may enter the data into the SIMS server 115.

Figure 1B:
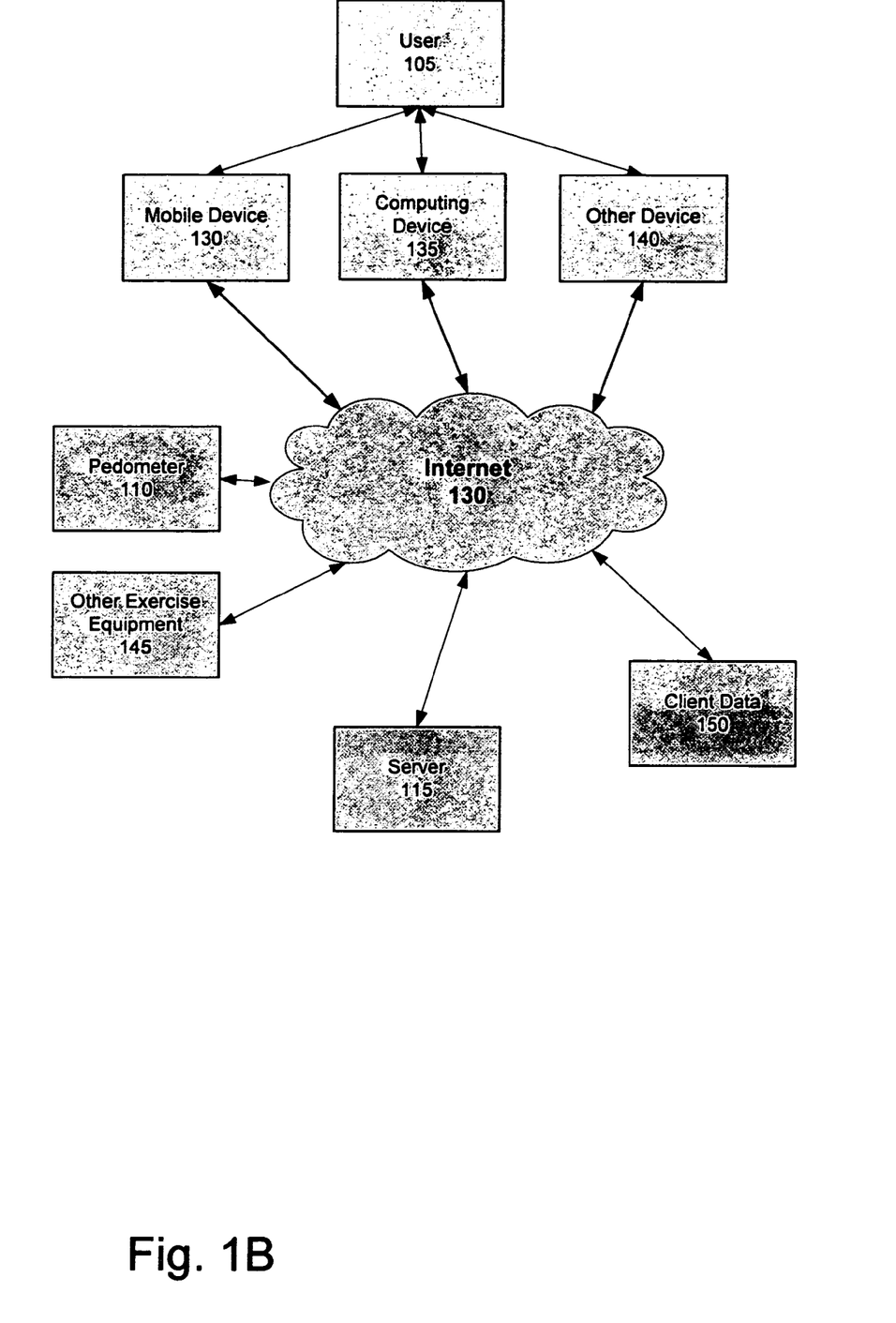
FIG. 1B is a block diagram of one embodiment of a network which may be used by the system.

FIG. 1B is a block diagram of one embodiment of a network which may be used by the system. The user 105 interacts with the system through a computing device 130. The computing device 130 may be a mobile phone, a step counting phone, a handheld device, a laptop, a computer, or any other device which can display goal data for the user. In one embodiment, the computing device 130, or another device 135, is used to automatically obtain activity/exercise data from the user. This data is sent via a network 130 to the server 115. In one embodiment, the network 130 may be a cellular network, wireless network, wired network, or other means.

In one embodiment, a user 105 can use multiple devices 130, 135, 140 to access the data. The data may be properly formatted for each type of device. For example, a small step counting phone having a monochrome display may simply display the current target, current achievement level, and the next target. A phone with a full color display may show the full progress graph, illustrating the user's approach or exceeding of each of the goals.

The data may be entered by the user 105 via one of the devices 130, 135, 140. Alternatively, one of the devices such as a pedometer 110, or another exercise device 145, may send data to the server 115. The pedometer 110 or exercise device 145 may connect to server 115 via one of the devices 130, 135, 140 of the user 105.

The user's data is stored in user data repository 150. In one embodiment, the user data repository 150 is a database. In one embodiment, the user data repository is a distributed database. The server 115 uses the data from the database to calculate daily targets for each user.

Figure 2:
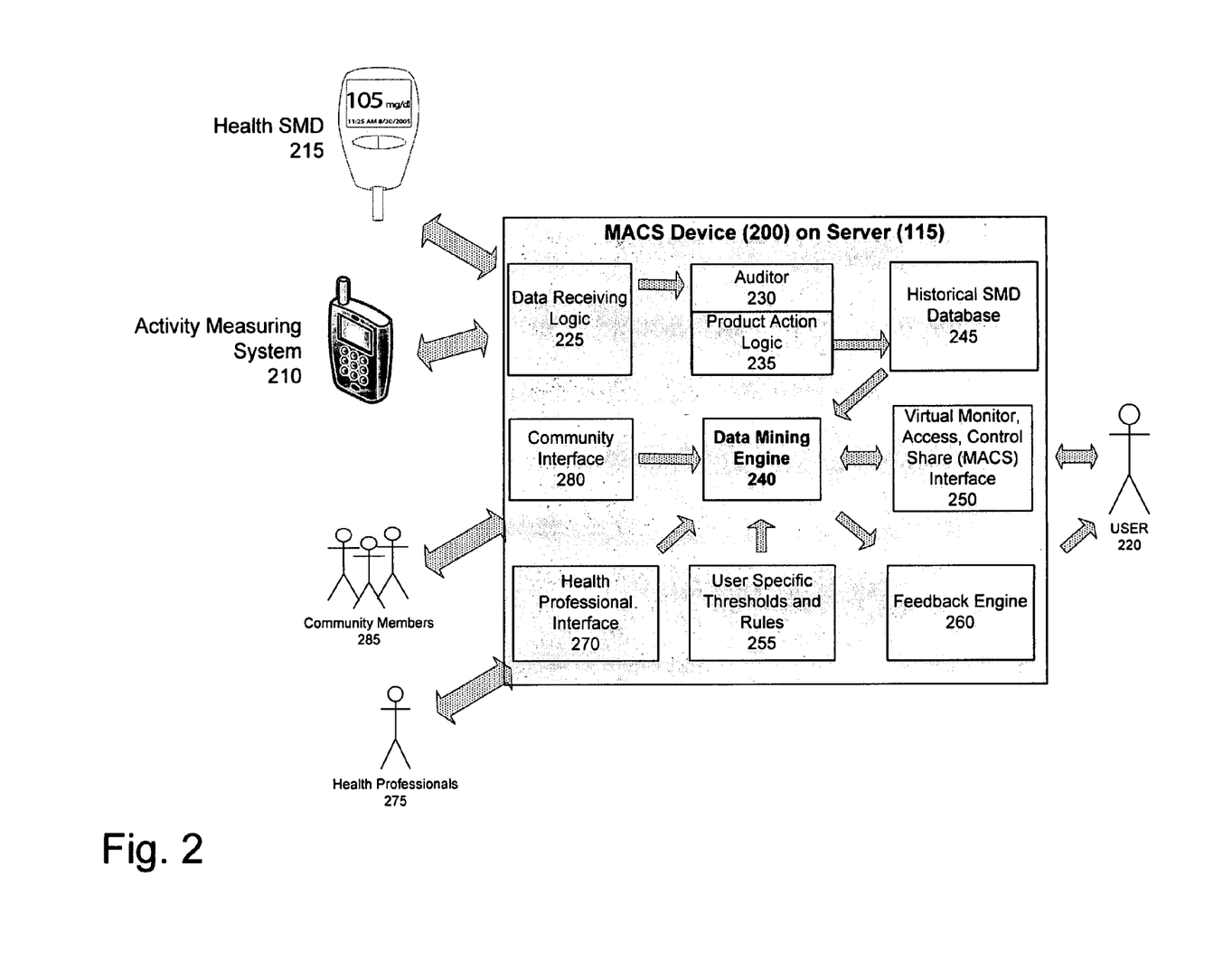
FIG. 2 is a block diagram of one embodiment of the MACS Device.

FIG. 2 is a block diagram of one embodiment of the MACS Device. The MACS device 200 includes a data receiving logic 225, to receive data from various devices. In one embodiment, devices include one or more health sensors, monitors, devices (SMDs) 215, as well as activity measuring systems 210. The activity measuring system 210 may be a pedometer, a device to measure distance traveled, exercise equipment capable of sending exercise data to the MACS Device 200. In one embodiment, the MACS device 220 may also receive health data including activity data from the user 220.

Auditor 230 reviews the data received from the devices and users. In one embodiment, if the data appears to be incorrect (for example 20,000 steps taken in 10 minutes), auditor 230 ensures that the incorrect data is not entered in the database 245. In one embodiment, auditor 230 is also designed to track when data is expected from the user or activity measuring system 210. In one embodiment, if expected data is not received, auditor 230 attempts to interface with the activity measuring system 210. In one embodiment, if the activity measurement system is turned off, the auditor 230 notifies the user through some other means. In one embodiment, the auditor 230 also collects data about the various types of activity measurement systems 210. In one embodiment, a product action logic 235 notifies manufacturers, distributors, and/or payers (i.e. insurance companies, hospitals, HMOs, etc.) if there are consistent problems with a certain type of activity measurement system 210. In one embodiment, feedback engine 260 is used for sending such notifications.

Once the data is verified by auditor 230, it is stored in the database 245. Data mining engine 240 utilizes this data to provide analysis, suggestions, feedback, etc. Data mining engine 240 includes the advanced exercise targeting logic (shown in FIG. 3). In one embodiment, data mining engine 240 and data from the historical database 245 are used to maintain a virtual SMD interface 250, which enables a user, healthcare provider, or other authorized individual to interact with the health SMD—in one embodiment including the activity measuring system 210—based only on the data within the MACS system 200. In one embodiment, the virtual SMD system may present an interface similar to the interface of the actual SMD which is being represented.

User specific thresholds and alert rules 255 enable the system to be customized per user. For example, in the context of the progress graph, a user may prefer to receive a reminder when he or she is 1000 steps behind the current goal level for the day. Another user may prefer to be reminded when he or she is only 100 steps behind. In one embodiment, the customization described above with respect to the user's behavioral pattern, is done by modifying the user specific thresholds and rules 255.

In one embodiment, the MACS system 200 also provides a separate interface for a community 280. The community interface 280 provides the user interaction with other users, to encourage activity, competition, and making activity a part of one's lifestyle. A health professional interface 270 enables a health professional to interact with the data in database 245. In one embodiment, health professionals—which may include doctors, nurse practitioners, insurance agents and others—may also send notices to the user via the MACS system. In one embodiment, the MACS system enables interactions between the user and such health professionals, and logs these interactions.

Figure 3:
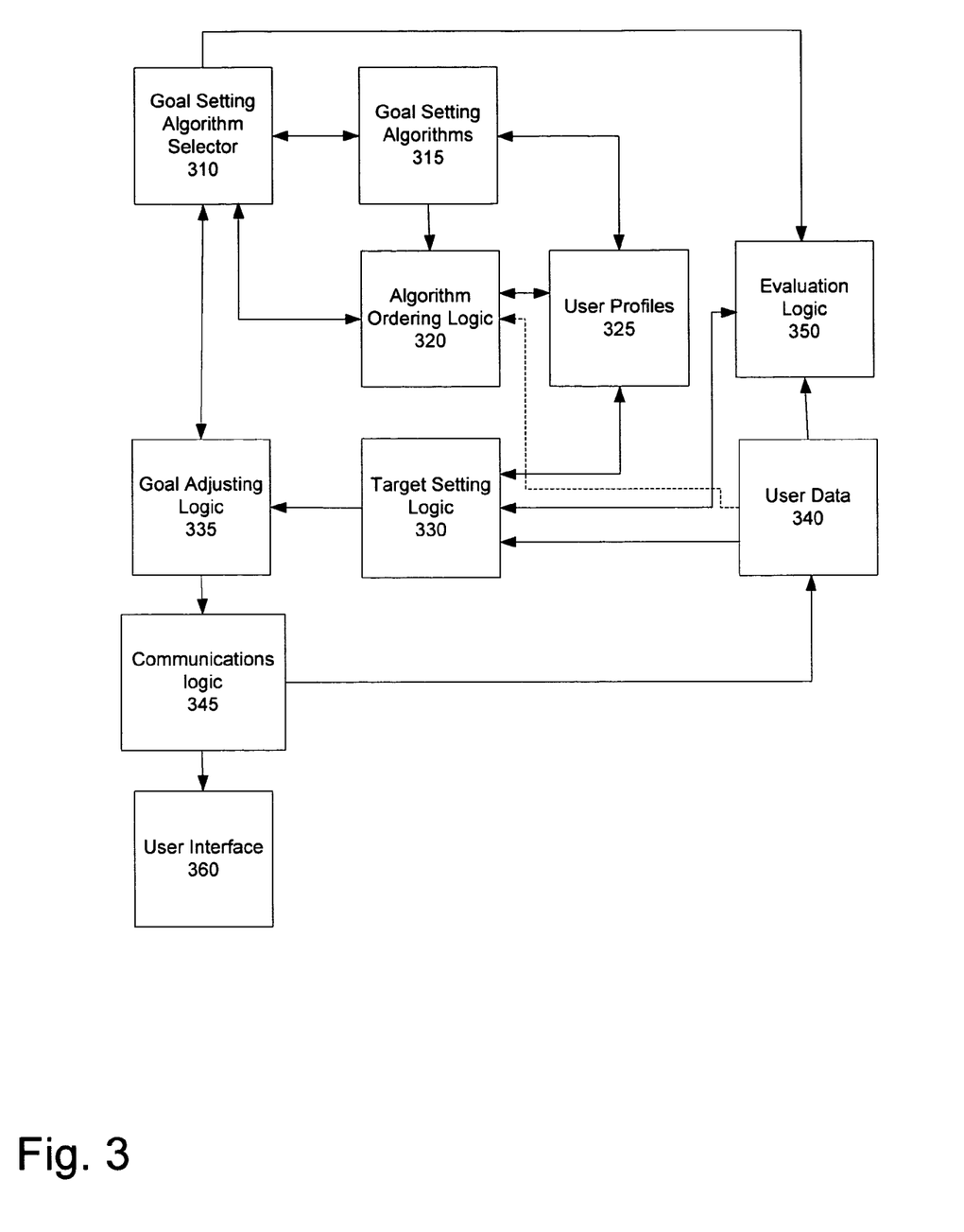
FIG. 3 is a block diagram of one embodiment of the goal setting logic.

FIG. 3 is a block diagram of one embodiment of the advanced exercise targeting logic. For simplicity, this is going to be described with respect to a walking/pedometer driven exercise regime. However, these targeting mechanisms may be used regardless of the type of exercise being evaluated.

The system includes a target setting logic 330 to set a raw target for exercise for a user. The raw target set by target setting logic depends on data from the user's profile, stored in user profiles 325, and on past user data, stored in user data 340. In one embodiment, user profiles 325 and user data 340 are both stored in a database. In one embodiment, the data may be stored in a single database.

This raw target is adjusted by goal adjusting logic 335, based on a goal setting algorithm selected for the user. Goal setting algorithm selector 310 selects which goal setting algorithm to use, to adjust the user's raw target. In one embodiment, the system includes a plurality of goal setting algorithms 315. In one embodiment, these algorithms are stored in a database. In one embodiment, an algorithm comprises one or more sub-algorithms. In one embodiment, the goal setting algorithms are stored in two parts. A plurality of sub-algorithms are stored, and then a plurality of goal setting algorithms are stored as pointers to the sub-algorithms which are part of that goal setting algorithm. Thus, for example, if there are sub-algorithm for set 1: A, B, C; set 2: D, E, F; and set 3: G, H, I, then a goal setting algorithm may be A:E:G.

Goal setting algorithm selector 310 selects one of the goal setting algorithms for a user. As will be described below in more detail, in one embodiment, a motivation analysis is performed based on success evaluation of prior goal setting algorithms and/or past user behavior. The other factors that may be used in selecting the goal setting algorithm may include one or more of: collective data about many different users, high activity times, low activity times, recent injuries, blood glucose levels, pre-diabetic conditions, interactions with health professionals, specifics about user's work and work environment, and other relevant data.

In one embodiment, the goal setting algorithms 315 are ordered for a user based on algorithm ordering logic 320. In one embodiment, algorithm ordering logic 320 creates an order for the particular user being evaluated, based on the user profile 325, and user data 340. In one embodiment, the algorithm ordering logic 320 is utilized when the user is initially evaluated, when new goal setting algorithms have been added, when the user profile changes, or when all of the goal setting algorithms have been evaluated.

In one embodiment, after a user has performed exercise, and user data has been collected, evaluation logic 350 evaluates the performance of the user compared to the goals. This evaluation is used to determine whether the goal setting algorithm works for the user or not. Collective data about many users also provides a correlation between a particular user profile and the success of a particular goal setting algorithm. That, in turn, is used by algorithm ordering logic 320 to determine which algorithm to test next for the user.

The final, adjusted, goal is sent to a user interface 360 via communications logic 345. Generally, the user interface 360 is located on a mobile system available to the user, for example a step counting phone, or similar mobile device.

In one embodiment, the user's performance data is also received through communications logic 345, and stored as user data 340. As noted above, this is used to set the raw target, as well as to select an appropriate goal setting algorithm.

FIG. 4 is an illustration of one embodiment of a progress graph showing goals throughout the day. The graph illustrates the user's current progress 405, in relationship to the day's total goal 410. In one embodiment, for pedometer data, the goal 410 includes a total step goal 410 and a total aerobic step goal 415.

In one embodiment, the progress graph further displays the achieved checkpoints 420, and unachieved checkpoints 425. The user has goals throughout the day. In one embodiment, goals are set on a fifteen minute increment. In another embodiment, goals are verified in a larger or smaller increment. In one embodiment, the system may note when the user has achieved a certain performance with bonus prizes 430. The bonus prize 430 may simply be an achievement marker attached to the user's name. In another embodiment, the bonus prize 430 may range from discounts to actual awards.

The progress graph illustrates the goals—here shown in dotted lines—as well as the user's progress—here shown as solid shapes. As can be seen, the daily goals set expectations throughout the day. This particular user, for example, has a short walk expectation between 8 a.m. and 9 a.m., likely a morning walk or jog. There is a second spurt of exercise around 5-6 p.m. These goal patterns are based on the user's actual past behavior, and motivational structure. For example, it is likely that this user usually has a short aerobic morning walk, and goes on his or her main walk of the day between 5 and 6 p.m. Thus, the goals are tailored to the user and designed to be achievable by the particular user.

Figure 5:
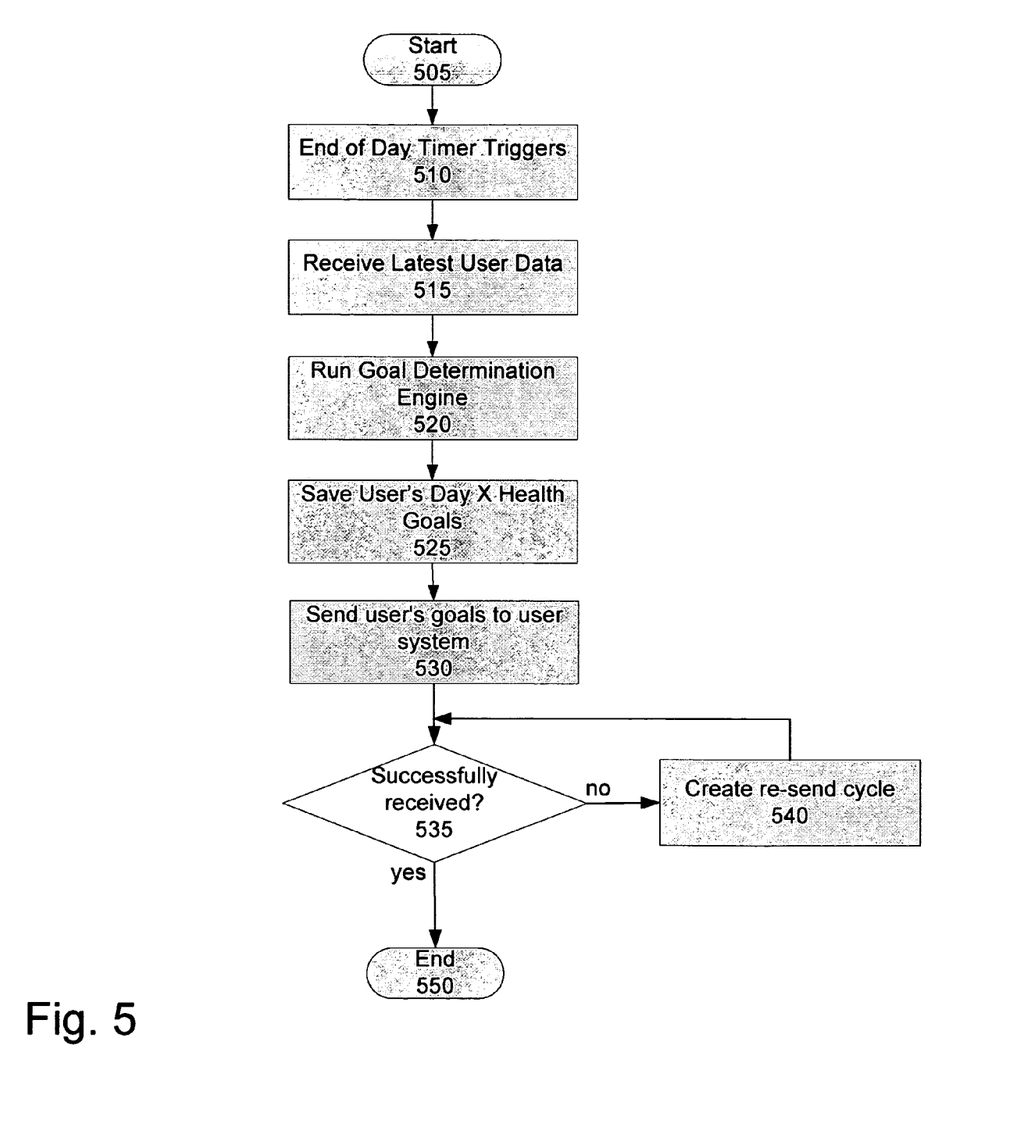
FIG. 5 is an overview flowchart of one embodiment of setting goals.

FIG. 5 is an overview flowchart of one embodiment of setting goals. The process starts at block 505. At block 510, the system is triggered to create new goals for a new day. In one embodiment, the timing may vary by user. In one embodiment, the timing is designed to do a final synchronization, to receive the latest user data 515. In one embodiment, this occurs after the last normal time of exercise for the user. For example, for a user who goes to sleep at 9 p.m. the synchronization may occur at 8:55, to ensure that the electronic devices for synchronization are still available. For a user who doesn't go to sleep until after midnight, the trigger may be at midnight. In one embodiment, the definition of "day" may be flexible per user. For someone working the nightshift, for example, a "day" may be from 3 p.m. until 7 a.m. In one embodiment a "day" is defined as the awake period within a 24-hour period of this particular user. Thus, in one embodiment, the "end of day" triggers, at block 510, occur at an appropriate time for this particular user's day.

At block 520, the goal determination engine is run. The goal determination engine utilizes the historical data from the user, as well as knowledge about the user's response to prior goals to set up daily goals.

At block 525, the user's goals are saved. In one embodiment, the user's goals are made available to the various devices the user utilizes during the day. For example, at bock 530, the goals may be sent to the user's step counting phone. In one embodiment, if the goals are not sent successfully, 535, a re-send cycle is created. The re-send cycle, in one embodiment, resends the data periodically. In one embodiment, depending on why the sending failed, the re-send cycle may vary. For example, if the device was not available—i.e. likely turned off or out of range—the re-send wait period would be longer than if the device received a garbled version of the data.

Once the data has been successfully received by the user's device(s), the process ends at block 550.

Figure 6:
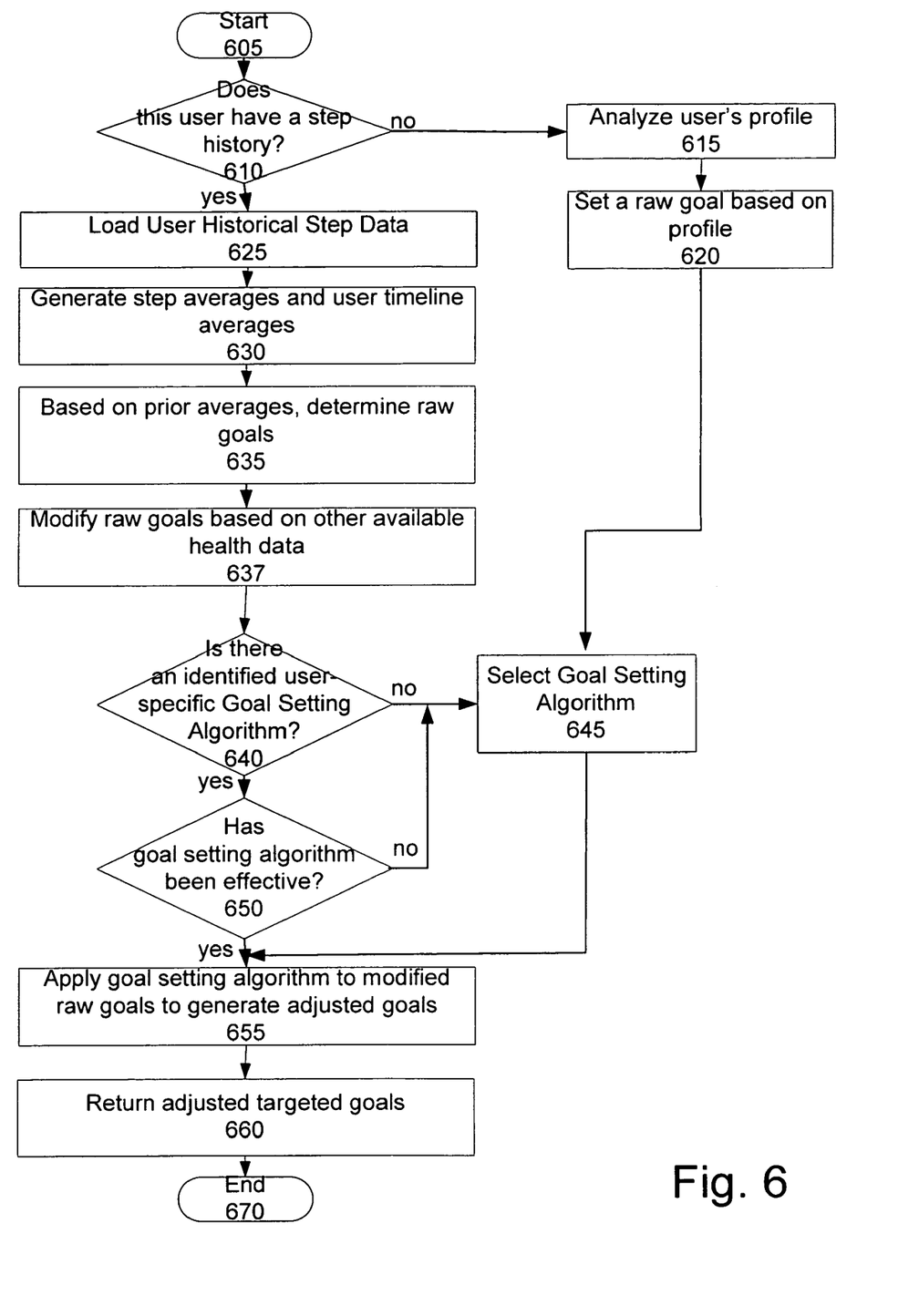
FIG. 6 is a flowchart of one embodiment of generating adjusted goals.

FIG. 6 is a flowchart of one embodiment of generating adjusted goals. The process starts at block 605. This process, in one embodiment, corresponds to block 520 in FIG. 5, and describes in more detail the goal determination engine's functions. For the purposes of this example, the exercise data will be assumed to be pedometer/step data. Of course, alternative data—i.e. data from other types of exercise measurements or devices, may be used.

At block 610, the process determines whether the user has a step history. If the user does not have a step history, the process continues to block 615. This indicates that the user is a new user.

At block 615, the user's profile is analyzed. The user's profile may include: age, BMI, geographic location, health conditions, overall fitness level, current exercise regime, and any other relevant data.

At block 620, a raw step goal is set for the user, based on the health profile. As noted previously, the present system collects data from numerous users. Furthermore, there are health goals based on the user's age and health condition which may be used. Thus, the system selects a raw goal that is commensurate with the user's expected performance levels. The process then continues to block 645, to select a goal setting algorithm.

If the user was found to have a step history, at block 610, the user's historical step data is loaded, at block 625. In one embodiment, the historical data may be uploaded from a different source. For example, if a user has been tracking his or her step data in a spreadsheet, in one embodiment, the user may upload this data to the system. Thus, in one embodiment, a user may have a step history even as a brand new user.

At block 630, the system generates step averages. In one embodiment, step averages are simply averages of all steps taken over the day. In another embodiment, the step averages may be calculated over time segments. In one embodiment, the step averages may differentiate between aerobic and non-aerobic steps. In one embodiment, timeline averages are also generated. The timeline averages indicate at what times approximately the user tends to take most of his or her exercise. For example, the timeline averages may simply provide a set of "high activity" and "low activity" time ranges.

At block 635, based on the prior averages, including step and timeline settings, a raw goal set is determined. In one embodiment, the raw goal set is very similar to the final goal set—shown in FIG. 4, for example. It includes steps at various time increments.

At block 637, the raw goals are modified, if appropriate, based on other available health data. For example, other available health data may include recent injuries, blood glucose levels after meals, pre-diabetic conditions, etc. The health data may have one or more adjustments associated with it. For example, for someone with a pre-diabetic condition, walking after a meal can help control blood glucose levels. Therefore, the system may adjust the walking goals to increase target goals after meals, etc.

Figure 7:
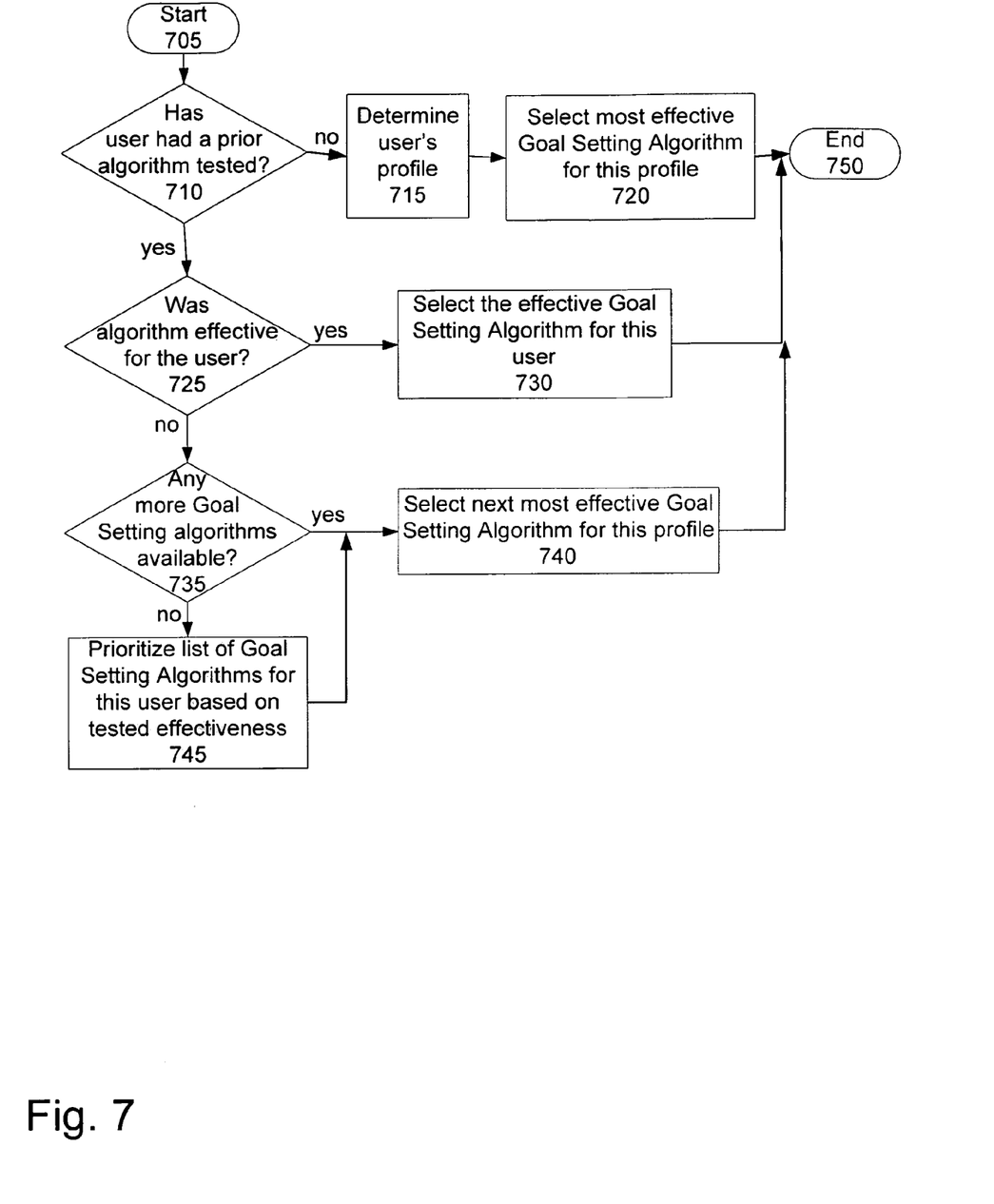
FIG. 7 is a flowchart of one embodiment of selecting a goal setting algorithm for the user.

At block 640, the process determines whether there is an identified user-specific goal setting algorithm. The goal setting algorithm makes adjustments to the raw goals based on knowledge about the user. If there is no identified user-specific goal setting algorithm selected at this time, the process continues to block 645, and a goal setting algorithm is selected. One embodiment of how this selection takes place is shown in FIG. 7. The process then continues to block 655.

If there is already a user specific goal-setting algorithm, the process continues to block 650. At block 650, the process determines whether the goal setting algorithm has been effective. In one embodiment, effectiveness is evaluated based on the success ratio of the user. In one embodiment, success ratio is evaluated on a per-checkpoint basis, i.e. how many of the daily checkpoints were met by the user.

If the goal setting algorithm has not been effective, the process continues to block 645, to select another goal setting algorithm. The process then continues to block 655. If the goal setting algorithm has been effective, the process continues directly to block 655.

At block 655, the goal setting algorithm is applied to the modified raw goals to generate adjusted goals. The adjusted goals are designed to change the displayed goals of the user, to help the user achieve the modified raw (real) goals.

The process, at block 660, returns the adjusted goals to the system. These are the goals, as described above with respect to FIG. 5, that are made available to the user, and used to evaluate user performance.

FIG. 7 is a flowchart of one embodiment of selecting a goal setting algorithm for the user. At block 705, the process determines whether the user has had a prior algorithm tested. If the user is brand new, there may not have been any algorithms tested to date for the user. If there have been no prior algorithms, the process continues to block 715.

At block 715, the user's profile is determined. In one embodiment, the same profile analyzed in determining raw step goals, as discussed above, is used. In one embodiment, whatever other relevant features are found through aggregate data analysis may be used. For example, the analysis may find that people who work in the medical field, or people who work the night shift, or people who work in cubicles tend to do better with certain types of goals. Such data may be included in the user profile, when available. Thus, all data known about the user may be part of this profile.

At block 720, the most effective goal setting algorithm for this profile is selected. As noted above, the system tracks goal setting algorithms' success rate for each user. Thus, after a time, for each user profile there is a 'most successful statistically' goal setting algorithm. The process then ends at block 750.

If the user has a prior algorithm, as determined at block 710, the process continues to block 725. At block 725, the process determines whether the algorithm was effective for the user. If so, at block 730 the known effective algorithm is selected for the user. The process then ends at block 750.

If the algorithm was not effective, as determined at block 725, the process continues to block 735. At block 735, the process determines if there are any goal setting algorithms that have not yet been tried & found ineffective for this user. If so, at block 740, the next most effective goal setting algorithm for this profile is selected. The process then ends at block 750.

If it is found that all goal setting algorithms have been tested, at block 735, the process continues to block 745.

At block 745, the set of goal setting algorithms which were tested for the user are prioritized, based on effectiveness. The system, in one embodiment, then resets the availability of goal testing algorithms' as tested at block 735. The process then continues to block 740, to select the most effective goal setting algorithm, from the ordered list created at block 745.

In one embodiment, after the system reaches block 745 once, the "list of available goal setting algorithm" is reset to the new customized list, based on prior effectiveness for this particular user. In one embodiment, after the system reaches block 745 twice, finding that none of the goal setting algorithms are available, the most effective algorithm is selected. In one embodiment, if in the meantime additional algorithms, sub-algorithms, or algorithm alternations have been implemented since the prior evaluation at block 745, the new/changed algorithms are evaluated, prior to selecting whichever algorithm is most effective.

Figure 8:
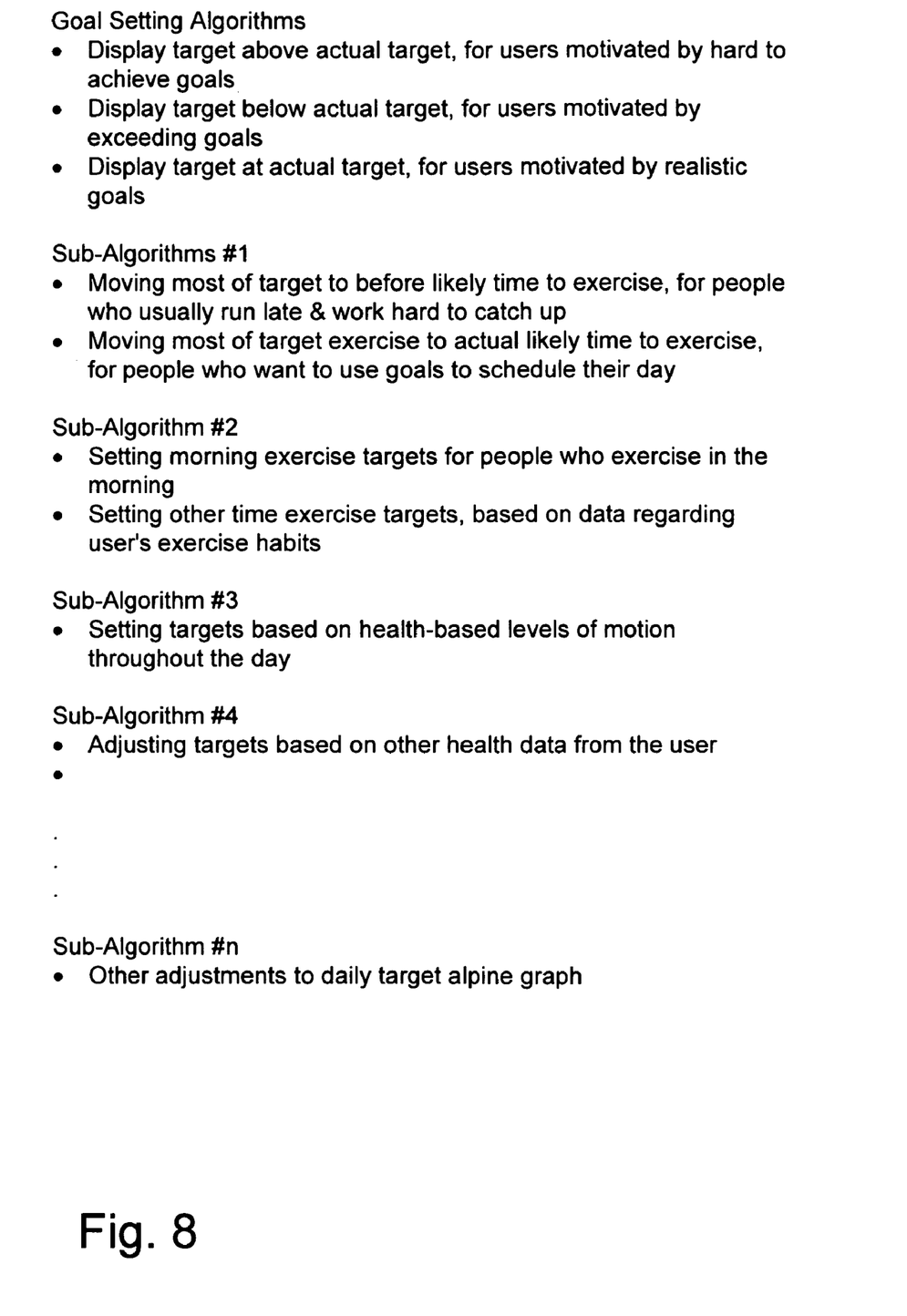
FIG. 8 is a chart of exemplary goal setting algorithms.

FIG. 8 is a chart of exemplary goal setting sub-algorithms. In one embodiment, each goal setting algorithm includes one or more of the listed sub-algorithms. For example, a complete algorithm may be:

Set actual target to increase by 100/steps over prior target, to ramp up exercise level for weightloss;
Set movement goals after lunch for control of blood glucose levels;
Set large exercise block target for evening based on exercise habits;
Display goal above actual target; and
Shift target time to earlier than actual target times.

Of course, for each user the actual sub-goals which are part of the complete goal setting algorithm may vary. For example, if the individual does not have diabetes or pre-diabetes, there may not be walking goals after meals, etc.

In the foregoing specification, the invention has been described with reference to specific exemplary embodiments thereof. It will, however, be evident that various modifications and changes may be made thereto without departing from the broader spirit and scope of the invention as set forth in the appended claims. The specification and drawings are, accordingly, to be regarded in an illustrative rather than a restrictive sense.

What is claimed is:

1. A method comprising:
   identifying with a computer a daily raw target exercise level for a user;
   applying a goal setting algorithm with a computer to adjust the daily raw target exercise level for the user, the adjustment made in accordance with a motivational analysis of the user, wherein the motivational analysis is based on at least one factor that incites the user to reach the daily raw target exercise level;
   displaying an adjusted target exercise level to the user, in order to achieve the daily raw target exercise level for the user; and utilizing at least one of a plurality of goal setting algorithms that adjust the daily raw target exercise level for the user.

2. The method of claim 1, further comprising:
   utilizing at least one of a plurality of goal setting algorithms, based on actual data from the user's performance.

3. The method of claim 1, further comprising:
   generating an ordering of goal setting algorithms based on a user profile; and
   for a new user, selecting a first goal setting algorithm based on the user's profile.

4. The method of claim 3, further comprising:
   evaluating a success of the goal setting algorithms based on a user's performance compared to the daily raw target exercise levels; and
   altering the goal setting algorithms for the user, when the goal setting algorithm is not a success.

5. The method of claim 1, wherein the adjusted target exercise level comprises a plurality of goals to be reached throughout the day.

6. The method of claim 5, wherein the display comprises a progress graph displaying a target number of steps at each moment during the day.

7. The method of claim 1, further comprising:
   selecting at least one of a plurality of goal setting algorithms for the user based on one or more of: a success evaluation of prior goal setting algorithms, past user behavior, collective data about many different users, high activity times, low activity times, recent injuries, blood glucose levels, pre-diabetic conditions, interactions with health professionals, specifics about the user's work, and specifics about the user's work environment.

8. A computer-implemented system to set exercise goals comprising:
   target setting logic to identify a daily raw target exercise level for a user;
   a goal adjusting logic to apply a goal setting algorithm to the daily raw target exercise level to create an adjusted daily target exercise level, the goal setting algorithm based in part on a motivational analysis of the user based on past behavior of the user;

a communications logic to send the adjusted target exercise level to the user, in order to achieve the daily raw target exercise level for the user; and a goal setting algorithm selector to select one of a plurality of goal setting algorithms that adjust the daily raw target exercise level for the user.

9. The system of claim 8, further comprising:

a goal setting algorithm selector to select one of a plurality of goal setting algorithms, based on actual data from the user's performance.

10. The system of claim 6, further comprising:

an algorithm ordering logic to order the plurality of goal setting algorithms based on a likelihood of effectiveness.

11. The system of claim 10, wherein for a new user the algorithm ordering logic utilizes a user profile, and orders the plurality of goal setting algorithms based on their effectiveness for a user of the same profile.

12. The system of claim 10, wherein for a user having recorded user data, the ordering logic utilizes the user data to select a most effective goal setting algorithm for the user.

13. The system of claim 10, further comprising:

an evaluation logic to evaluate a success of the goal setting algorithm based on a user's performance compared to the daily raw target exercise levels; and the goal setting algorithm selector to select another goal setting algorithm for the user, when the selected goal setting algorithm is not a success.

14. The system of claim 8, wherein the adjusted target exercise level comprises a plurality of goals to be reached throughout the day.

15. The system of claim 14, wherein a display comprises a progress graph displaying a target number of steps at each moment during the day.

16. The system of claim 8, wherein the motivational analysis of the user further comprises one or more of: a success evaluation of prior goal setting algorithms, collective data about many different users, high activity times, low activity times, recent injuries, blood glucose levels, pre-diabetic conditions, interactions with health professionals, specifics about the user's work, and specifics about the user's work environment.

17. A system to provide goals for exercise comprising:

computer adjusted goal adjusting logic to generate a target step count for a day;

a user interface to provide the target step count to a user;

a display to show a two-dimensional progress graph including the target step count throughout the day, the progress graph showing a current achievement of the user and progress toward the target step count in relationship to a timeline for the day, and a plurality of goals to be reached throughout the day; and the goal adjusting logic is selected from a plurality of stored goal setting algorithms that adjust the daily raw target exercise level for the user.

18. The system of claim 17, wherein the progress graph comprises a continuous set of goals at any time of day.

19. The system of claim 18, further comprising:

the goal adjusting logic further to adjust the continuous set of goals based on at least one subgoal for the user, to encourage the user to complete the continuous set of goals.

20. The system of claim 19, wherein the subgoals of the user comprise one or more of the following: ramping up to a final exercise goal, exercising at particular times of day, displaying a target level above/below/at an actual target, setting exercise times before/after/at actual target times.

21. The system of claim 19, wherein the subgoals of the user are determined based on historical performance of the user.

* * * * *